United States Patent [19]

Nomoto et al.

[11] Patent Number: 5,015,097

[45] Date of Patent: May 14, 1991

[54] METHOD FOR INSPECTING FILLED STATE OF VIA-HOLES FILLED WITH FILLERS AND APPARATUS FOR CARRYING OUT THE METHOD

[75] Inventors: Mineo Nomoto, Yokohama; Takanori Ninomiya, Hiratsuka; Hiroya Koshishiba; Toshimitsu Hamada, both of Yokohama; Yasuo Nakagawa, Chigasaki, all of Japan

[73] Assignee: Hitachi, Ltd., Tokyo, Japan

[21] Appl. No.: 416,934

[22] Filed: Oct. 4, 1989

[51] Int. Cl.$^5$ .................. G01B 11/00; G01N 21/00; G06K 9/00

[52] U.S. Cl. ................................. 356/394; 356/237; 382/8

[58] Field of Search ............... 356/237, 394; 358/101, 358/106; 382/8; 364/550, 552, 488, 489, 490, 491

[56] References Cited

FOREIGN PATENT DOCUMENTS 58-92904 2/1983 Japan .
58-153328 9/1983 Japan .
60-22611 2/1985 Japan .
61-17049 1/1986 Japan .

OTHER PUBLICATIONS

W. E. Blanz, J. L. C. Stanz, E. B. Hinkle, "Image Analysis Methods for Solder Ball Inspection in Integrated Circuit Manufacturing", Proc. IEEE Int. Conf. on Robotics & Automation, pp. 509–514, 1987.

John R. Kender, Earl M. Smith, "Shape from Darkness: Deriving Surface Information from Dynamic Shadows", Proc. of 1st Int. Conf. Compt. Vision, pp. 539–546, 1987.

Singo Sekiguchi, Mitsutaka Ito, Shinichi Uno, "Apparatus for Inspecting Devices Mounted on Circuit Board (Chip Checker)", Papers of 2nd Symposium of Image-Sensing Technics in Industry, pp. 291–294, Jul. 1987.

Primary Examiner—F. L. Evans
Assistant Examiner—K. P. Hantis
Attorney, Agent, or Firm—Kenyon & Kenyon

[57] ABSTRACT

A method for inspecting the filled state of a plurality of via-holes which pass through a non-conductive circuit board and are filled with a conductive substance and an apparatus for carrying out the method are disclosed.

The surface of the circuit board is illuminated in two directions to generate shadows depending on the concave or convex state of the fillers in a plurality of via-holes. An optical image of the illuminated surface of the circuit board is detected. Each edge of the two shadow areas, which exist in the detected optical image and are generated in one via-hole by light irradiation in two directions, is detected. Whether the filler in this one via-hole is in the concave state or convex state is identified according to the mutual position relationship of the detected edges. The length of each shadow area is detected, and whether the concave state or convex state of the filler is within a predetermined allowance is decided according to the detection results. The area of the image of the filler is detected according to differences between the brightness of the board surface or of the via-hole wall and the brightness of the filler in the via-hole in the detected optical image, and whether the filler is lacking or not is decided according to the detection result.

18 Claims, 16 Drawing Sheets

| | GOOD | CONCAVE DEFECT | CONVEX DEFECT | LACK OF FILLER DEFECT | BLOTCH DEFECT | BLOB DEFECT |
|---|---|---|---|---|---|---|
| FIG. 2(a) SECTIONAL VIEW OF VIA-HOLE | ILLUMINATION, FILLER, GREEN SHEET | SHADOW, ILLUMINATION | SHADOW, ILLUMINATION | BRIGHT, ILLUMINATION | | PLAN VIEW OF FILLER, BLOB |
| FIG. 2(b) DETECTED IMAGE | ○ | ○ | ○ | ○ | ○ | ○ ∘ |
| FIG. 2(c) IMAGE SIGNAL | GREEN SHEET, FILLER, $V_{H1}$, $V_{H2}$ | SHADOW | SHADOW | | | |
| FIG. 2(d) BINARY IMAGE | $V_{H1}$: AREA $SH_1$ PERIMETER $\ell$, $L_X$, $L_Y$; $V_{H2}$: NONE | AREA $SH_2$ | ∘ | ○ | ○ | ○ ∘ |
| FIG. 2(e) EXAMPLES OF CRITERIA | $SH_1 \fallingdotseq SH_0$ $SH_0$: REFERENCE VALUE $SH_2=0$ | $SH_1 \fallingdotseq SH_0$ $SH_2 > 0$ | $SH_1 > SH_0$ $SH_2 > 0$ | $SH_1 < SH_0$ | $SH_1 > SH_0$ $\ell > \ell_0$: REFERENCE VALUE | $SH_1 > SH_0$ $\ell > \ell_0$ |

$V_{H1} = \alpha \times Hmin + (1-\alpha) Hmax \quad 0 < \alpha < 1$
$V_{H2} = \beta \times Hmin \quad 0 < \beta < 1$

H: LENGTH OF ONE HORIZONTAL SCANNING LINE

ORDER OF IMAGE DETECTION →

265 VIA-HOLE

METHOD FOR INSPECTING FILLED STATE OF VIA-HOLES FILLED WITH FILLERS AND APPARATUS FOR CARRYING OUT THE METHOD

BACKGROUND OF THE INVENTION

The present invention relates to a method and apparatus for inspecting the filled state of via-holes filled with fillers, which are formed to electrically connect circuits on the front and back sides of a printed circuit board (a ceramic printed circuit board included).

An inspection method for via-holes of a translucent printed circuit board, which is made of polyimide, with copper circuits is indicated in Japanese Patent Application Laid-Open No. 61-17049. A detection method for a defective filling state of general fillers is indicated in Japanese Patent Application Laid-Open No. 55-118753.

Detection methods for the height of an object by measuring the shadow length of the object which is irradiated by light slantwise are indicated, for example, in Japanese Patent Application Laid-Open Nos. 60-22611 and 58-92904.

The techniques mentioned above cannot identify whether an object is protruded or sunk under a datum plane nor detect a defective filling state of fillers in each via-hole.

SUMMARY OF THE INVENTION

An object of the present invention is to provide a via-hole filled state inspection method and its apparatus, by which a concave defect or a lack of filler defect can be distinguished and detected from other defects Another object of the present invention is to provide a via-hole filled state inspection method and its apparatus, by which the filled state of fillers in each via-hole of a circuit board can be automatically inspected at a high speed.

The above objects are accomplished by the present invention providing a method for inspecting the filled state of via-holes of a circuit board filled with fillers, which comprises the steps of detecting an optical image of a surface of a circuit board, detecting the concave or convex state of the filler in each via-hole from each filler image of the via-holes in the detected optical image, and deciding whether the filler is in the concave or lack state on the basis of the detection result. The above objects are accomplished by the present invention providing an apparatus for inspecting the filled state of via-holes of a circuit board filled with fillers, which comprises an image detection circuit for detecting an optical image of the surface of each circuit board, a filled state detection circuit for detecting the concave or convex state of the filler in each via-hole from each filler image of the via-holes in the detected optical image, and a decision circuit for deciding whether the concave or lack state of the filler is within a predetermined allowance on the basis of the detection result.

DETAILED DESCRIPTION OF THE INVENTION

Via-holes, which are formed to electrically connect the circuits on the front and back sides of each layer of a multi-layer printed circuit board which is made of ceramics or others, or the printed circuits on the layers, are filled with a conductive substance such as tungsten or molybdenum. However, the filled state of each via-hole filled with a filler is not always satisfactory; for example, the filler is protruded from the surface of the ceramic layer or sunk below the layer surface due to a lack, or a part of the filler is missing, or an unnecessarily large amount of filler is formed on the layer surface. These defects should be strictly inspected because they may cause damage to the electrical connections, resulting in an extreme reduction in the reliability of printed circuit boards. For that purpose, a defective shape of the filler in each via-hole (for example, a concave defect, convex defect, lack of filler defect, blotch defect, or blob defect shown in FIG. 2) should be detected. For green sheets constituting a multi-ceramic layer printed circuit board (each layer before multilayering is called a "green sheet"), the concave defect and the lack of filler defect should be detected more sensitively than the other defects (see FIG. 2) because they are dangerous defects which may cause the failure in conduction. The convex, blotch, and blob defects may cause a short-circuit. If they are detected strictly in the same way as the concave defect or lack of filler defect, circuit boards, which can be considered as acceptable products, may be detected as defective products. When identifying and detecting the defects shown in FIG. 2, therefore, the detection sensitivity should vary with the defect type. Each green sheet constituting a multi-ceramic layer printed circuit board is provided with more than 10000 via-holes, and the filled state of each via-hole filled with a conductive substance should be automatically inspected precisely enough to detect defects and at a satisfactory speed. The present invention can satisfy such a request.

Descriptions of the function of the present invention follow. FIG. 2(a) shows the filled state of a via-hole filled with a filler. There are five defects specified, a concave defect, convex defect, lack of filler defect, blotch defect, and blob defect. FIGS. 2(b) and 2(c) show detected images of a via-hole by oblique illumination and image signals. The image signal level of each shadow generated by a concave or convex is lower than that of the filler of the via-hole. The use of a binary image, binarized by a threshold value $VH_2$ detecting only a shadow, to detect a concave or convex allows a concave or convex defect to be distinguished from another defects. To detect a lack of filler defect, a binary image binarized by a threshold value $VH_1$ near the center of the image signal level can be used. To detect a micro blob defect, a binarizing threshold value close to a signal level of layer image may be newly set. The defects described later can be detected from a binary image obtained by two or more binarizing threshold values mentioned above.

Descriptions of the principle of identifying a concave or convex and detecting a concave or convex defect follow. FIG. 3(a) and 3(b) show shadows generated by oblique illumination to a specific object.

The Figure shows that the left edge of the shadow generated by the left illumination corresponds to the location of the drop in level from the left to right of the object, and the right edge of the shadow generated by the right illumination corresponds to the location of the drop in level from the right to left of the object. Therefore, the concave or convex state of the object can be identified by the position relationship between the left edge (hereinafter called the −edge) of the shadow by the left illumination and the right edge (hereinafter called the +edge) of the shadow by the right illumination as shown in FIGS. 3(a) and 3(b). When the +edge and the −edge are arranged in this order from left to right in the Figure, the filler surface is convex. When the −edge and the +edge are arranged in this order from left to right in the Figure, the filler surface is concave. The shadow length between the left end of the image and the first +edge and the shadow length between the last −edge and the right edge of the image correspond to the amount of convexity. The shadow length between the −edge and the +edge corresponds to the amount of concavity. Assuming that length of each shadow is 1, the angle between the datum plane and the illumination axis is $\theta$, and each shadow is to be observed and detected perpendicularly to the datum plane, the height h from the datum plane when the object is convex is as follows:

$$h = 1 \tan \theta$$

Assuming that the concave width is d When the object is concave:

$$l = \min (d, h/\tan \theta)$$

The symbol ( ) in the above expression means that the smaller of the two elements in the parentheses h cannot be obtained uniquely from 1. For detection of via-hole defects, d and h are often set as defect detection reference values. If an appropriate value is selected for $\theta$, a value corresponding to the degree of a concave defect can be obtained from 1. Therefore, no problems are caused by defect detection.

FIG. 4 shows the detection principle of a lack of filler defect. When a via-hole having a lack of filler is detected by oblique illumination, the via-hole wall detected is brighter than the filler. As a result, in a binary image (1) binarized at a binarizing level (1) in the Figure, the area of the filler detected is smaller than that of a via-hole filled with the filler up to the green sheet surface. In the case that the wall of via-hole having a lack of filler is detected brighter than the green sheet surface and the image signal is binarized at a binarizing level (2), a binary image (2) is detected only when a lack of filler defect occurs. By comparing the area or diameter of a detected image, which is binarized by using the binarizing levels (1) and/or (2), with the reference value, a good product or the lack of filler defect can be distinguished from a defective product or another defects.

For a blotch defect, the detected image in FIG. 2 (b) shows that the area of the filler detected is larger than that of the good product. When a comparison shows that the area or perimeter of the detected image is larger than the reference value, the filler can be identified as a defective one. In the case of a blob defect, a good product or the blob defect can be distinguished from a defective product or another defects by comparing the area, perimeter, or diameter of the detected image of the filler of a via-hole with the reference value in the same way as a blotch defect.

BRIEF DESCRIPTION OF THE DRAWINGS

FIGS. 2(a), 2(b), 2(c), 2(d), and 2(e) show a part of the principle of the inspection method of the present invention.

DETAILED DESCRIPTION OF PREFERRED EMBODIMENTS

Figure 1:
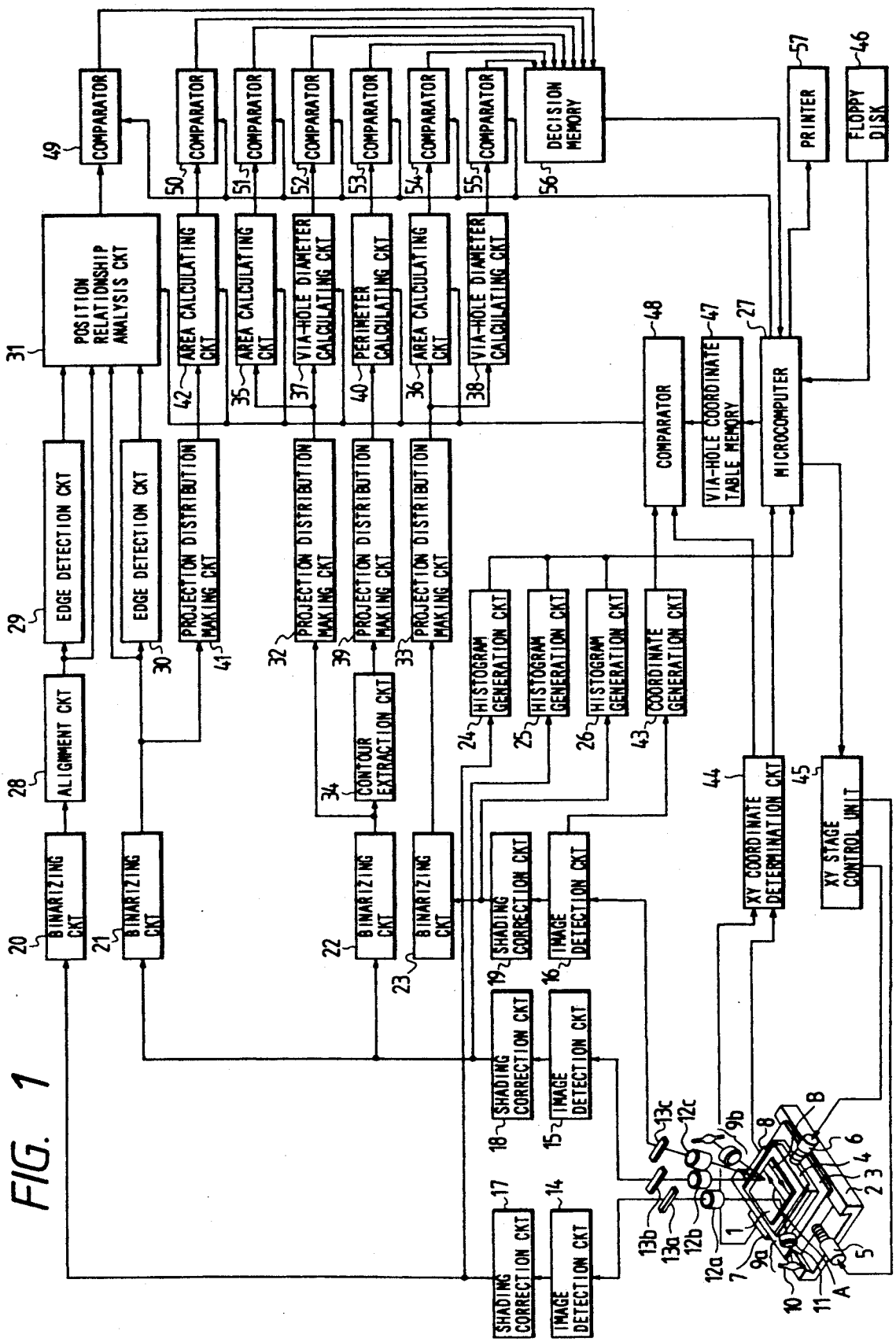
FIG. 1 is a block diagram indicating an example of an inspection apparatus for carrying out the method by the present invention.

FIG. 1 is a block diagram indicating an example of an apparatus for inspecting the filled state of a via-hole, which is provided to carry out the method according to the present invention. On a stage base 2 in FIG. 1, an X stage 4 is set via a Y stage 3 to configure an XY stage. A green sheet 1 which is to be inspected is mounted on the X stage 4. The X stage 4 and Y stage 3 are connected to X-axis drive unit 6 and Y-axis drive unit 5 which are external drive units, so as to be moved in the X and Y directions respectively. The movement distances of X stage 4 and Y stage 3 are measured by a linear scale for X-axis 8 and linear scale for Y-axis 7.

The green sheet 1 is illuminated obliquely by a parallel light beam illumination source 9a. An image of this portion, which is viewed from vertically upper is detected by a line sensor 13a via lens 12a. The plane which is formed by the optical axes of the illumination and detection systems is perpendicular to the surface of the object to be detected. The detection area of line sensor 13a is perpendicular to this plane.

A portion, which is in parallel with and at a distance of D from the detection area of line sensor 13a, is illuminated obliquely in the reverse direction by a parallel light beam illumination source 9b. An image of this portion, which is viewed from vertically upper point, is detected by a line sensor 13b via lens 12b. An image of the portion, which is obliquely illuminated by the parallel light beam illumination source 9b and is viewed from obliquely upper point, is detected by a line sensor 13c via lens 12c. Illumination source 9a should be designed to illuminate the detection area of line sensor 13a and illumination source 9b should be used to illuminate the detection areas of line sensors 13b and 13c. By moving the detection object 1 horizontally in a direction which is not in parallel with the primary scanning direction of line sensors 13a, 13b, and 13c, two-dimensional images can be obtained by line sensors 13a, 13b, and 13c via image detection circuits. The output data from sensors 13a, 13b, and 13c are inputted via shading correction circuits 17, 18, and 19 to binarizing circuits 20, 21, 22, and 23 and to histogram generation circuits 24, 25, and 26. The histogram generation circuits 24, 25, and 26 calculate the frequency of the detected image signal level to determine the threshold values mentioned above. The output data are inputted to a microcomputer 27, and the threshold values $VH_2$, $VH_1$, and $VH_3$ of binarizing circuits 20, 21, 22, and 23 can be determined by executing operations. The binarizing circuits 20 and 21 detect a shadow generated on the green sheet or the filler. The output data are corrected so as to compensate a difference of the line sensor detection locations by an alignment circuit 28, resulting in that line sensors 13a and 13b detect images produced by illuminations in different directions simultaneously.

Edge detection circuits 29 and 30 detect the +edge and the −edge of shadow areas. A position relationship analysis circuit 31 analyzes the position relationship between the +edge and the −edge, and detects and outputs the lengths of the shadows corresponding to the concave and convex. The output data from binarizing circuits 22 and 23 are inputted to projection distribution making circuits 32 and 33 and to a contour extraction circuit 34. The projection distribution making circuits 32 and 33 create horizontal and vertical (X and Y axes) projection distribution curves by binarizing signals. The area and diameter of the via-hole filler can be calculated from the distribution by area calculating circuits 35 and 36 and by via-hole diameter calculating circuits 37 and 38. The contour extraction circuit 34 extracts the contour of the via-hole filler by binarizing signals. The extracted contour signal is inputted to a projection distribution making circuit 39, and horizontal or vertical projection distribution is created. The perimeter of the via-hole filler is calculated from the distribution by a perimeter calculating circuit 40. The output data from binarizing circuit 21 is inputted to a projection distribution making circuit 41, and the shadow area is calculated from the distribution for each via-hole by an area calculating circuit 42.

A coordinate generation circuit 43 is supplied with a clock pulse of sensor 13a, 13b, or 13c from an image detection circuit 14, 15, or 16, and creates scanning position coordinates of the sensor. An XY coordinate determination circuit 44 is supplied with the output data from the linear scale for X-axis 8 and linear scale for Y-axis 7, and detects the position coordinates of sensor 13a, 13b, or 13c. The microcomputer 27 is designed so that it controls the X-axis drive unit 6 and Y-axis drive unit 5 via XY stage control unit 45 and is supplied with the position data of sensor 13a, 13b, or 13c from the XY coordinate determination circuit 44. A floppy disk 46 stores the design data (via-hole position, diameter, pitch, etc.) of the via-holes formed on the green sheet 1. The data is inputted to the microcomputer 27, and the X stage 4 and Y stage 3 are driven according to it. The via-hole position coordinates are inputted to a via-hole coordinate table memory 47 from the microcomputer 27. The contents of via-hole coordinate table memory 47 are compared with the output data of coordinate generation circuit 43 and XY coordinate determination circuit 44 by a comparator 48. A signal is outputted whenever the detection of a via-hole image is detected, and the position relationship analysis circuit 31, area calculating circuits 35, 36, and 42, via-hole diameter calculating circuits 37 and 38, and perimeter calculating circuit 40 are activated. The output data from position relationship analysis circuit 31, area calculating circuits 35, 36, and 42, via-hole diameter calculating circuits 37 and 38, and perimeter calculating circuit 40 are compared with the reference values, which are set by the microcomputer 27, by comparators 49, 50, 51, 52, 53, 54, and 55 to decide whether the filled state is acceptable or rejected. The output data from comparators 49, 50, 51, 52, 53, 54, and 55 are written into a decision memory 56 according to the corresponding coordinates of a via-hole coordinate table memory 47. The microcomputer 27 is supplied with the contents of decision memory 56 and outputs the decision to a printer 57.

When inspecting the filled state with this apparatus, the green sheet 1 is moved back and forth in the directions of the arrows A and B against objective lenses 12a and 12b to scan the entire surface sequentially. To move the green sheet 1 in the directions of the arrows A and B, the microcomputer 27 controls the X-axis drive unit 6 and Y-axis drive unit 5 via XY stage control unit 42.

The illumination method has an advantage that shadow images can be easily picked up by using a mercury lamp or a xenon lamp, which is a point illumination source, as illumination source 10 and generating a parallel light beam for illumination by condenser lens 11 to minimize diffraction phenomena.

Figure 5A:
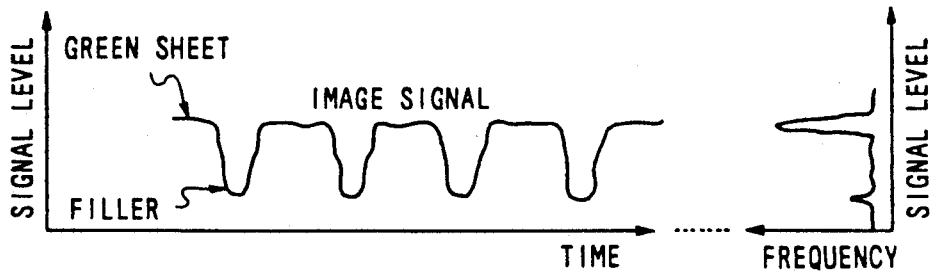
FIGS. 5(a) and 5(b) illustrate a method of determining threshold values to be used for binarizing an image signal of the inspection apparatus in FIG. 1.
Figure 5B:
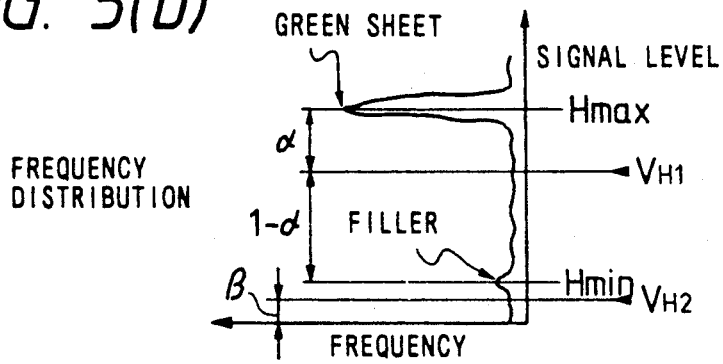

In the apparatus with the configuration mentioned above, a detected image signal is inputted to the shading correction circuit 17, 18, or 19 to correct uneven illumination or uneven sensitivity of line sensor 13a, 13b, or 13c. The shading correction circuits 17, 18, and 19 are, for example similar to the one indicated in Japanese Patent Application Laid-Open No. 58-153328. The shading-corrected image signal is binarized by the binarizing circuit 20, 21, 22, or 23 according to the binarizing threshold value $VH_2$, $VH_1$, or $VH_3$. The binarizing threshold values can be determined as follows. From the image signal detected as shown in FIG. 5(a), the frequency distribution is determined as shown in FIG. 5(b). A signal level $H_{max}$ indicating the brightness of the green sheet surface and a signal level $H_{min}$ indicating the brightness of the filler are determined from the distribution curve. The binarizing levels VH$_1$ and VH$_2$, which are threshold values, are determined by executing operations according to those output data. These operations are performed by histogram generation circuits 24, 25, and 26 and the microcomputer 27 shown in FIG. 1. These binarizing levels may be determined with a green sheet to be inspected before starting the automatic inspection.

From the images of the via-hole filler and of the shadows which are binarized by the method mentioned above, the position relationship of the shadow edges is analyzed for each via-hole, and the lengths of the shadow corresponding to the concave and of the shadow corresponding to the convex, the areas of the shadows, and the area, perimeter, and diameter of the via-hole filler are detected to decide defects.

Detailed descriptions of the detection method for the amount of concavity and the amount of convexity by identifying a concave and convex follow. The binarizing circuits 20 and 21 are used to obtain binarizing signals to detect shadows generated in the green sheet or filler. To correct a difference in the detection position between the two line sensors 13a and 13b, the signal from one of the line sensors is delayed by the alignment circuit 28 as if the line sensors simultaneously detect images produced by illuminations in different directions. A video memory operating as an FIFO (First-In First-Out) memory may be used as the alignment circuit 28. The edge detection circuits 29 and 30 detect the +edge or the −edge of each shadow area. Assuming that the input signal values which are vertically adjacent to each other are vi(i) and vi(i+1) and the output signal value is v$_o$(i), for the +edge:

$$v_o(i) = vi(i).\overline{vi(i+1)}$$

For the −edge:

$$v_o(i) = \overline{vi(i)}.vi(i+1)$$

where "−" indicates negation and "." indicates a logical product. Each image signal should be binarized so that it is 1 in the shadow area (dark area) and 0 in another area (bright area).

Figure 3A:
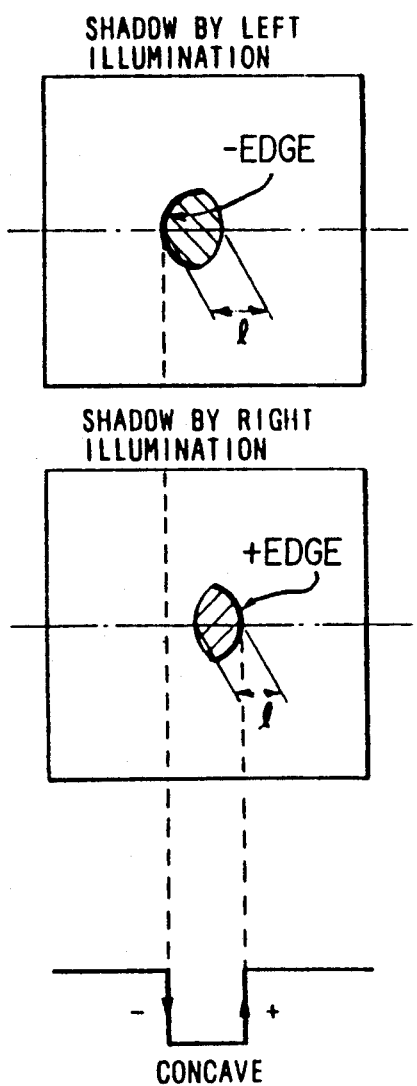
FIGS. 3(a) and 3(b) show the principle of detecting a concave or convex state which is specified by the inspection method provided by the present invention.
Figure 3B:
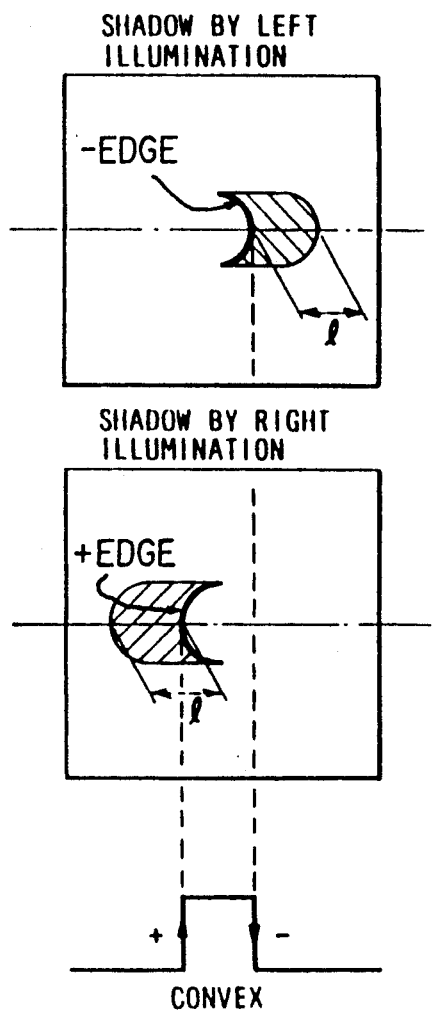
Figure 4:
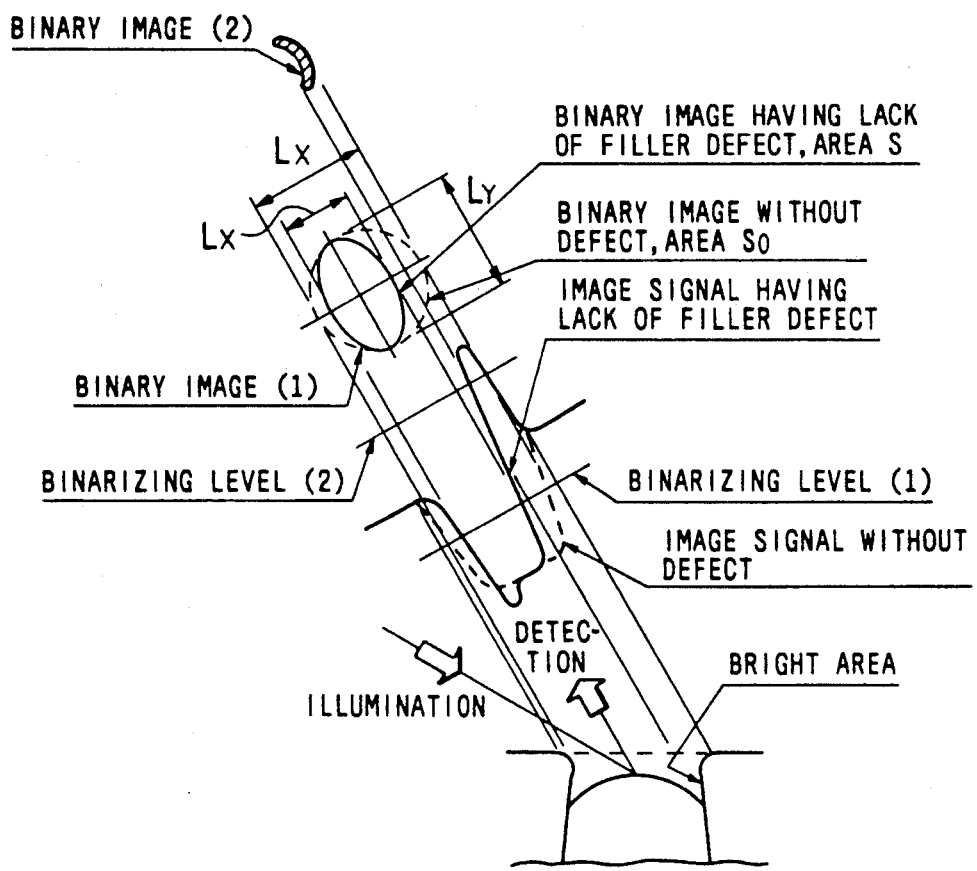
FIG. 4 shows the principle of detecting a lack of filler which is specified by the inspection method provided by the present invention.

The position relationship analysis circuit 31 analyzes the position relationship between the +edge and the −edge, and detects and outputs the lengths of the shadow corresponding to the concave and of the shadow corresponding to the convex. As shown in FIGS. 3(a) and 3(b) for the binary image of the shadow by the right illumination, the maximum length of the shadow between the left end of the image and the +edge is detected as amount of convexity 1, and the maximum length of the shadow between the −edge and the +edge is detected as amount of concavity 1. For the binary image of the shadow by the left illumination, the maximum length of the shadow between the −edge and the right end of the image is detected as amount of convexity 2, and the maximum length of the shadow between the −edge and the +edge is detected as amount of concavity 2.

Figure 6A:
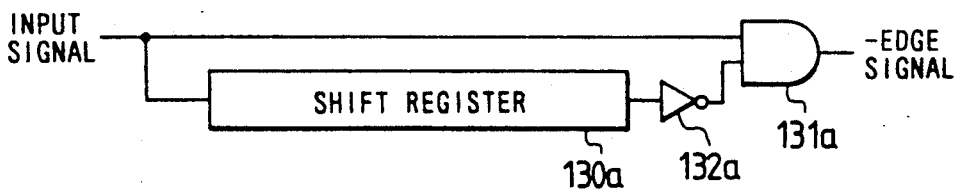
FIGS. 6(a) and 6(b) show examples of edge detection circuits to be used for the inspection apparatus in FIG. 1, respectively.
Figure 6B:
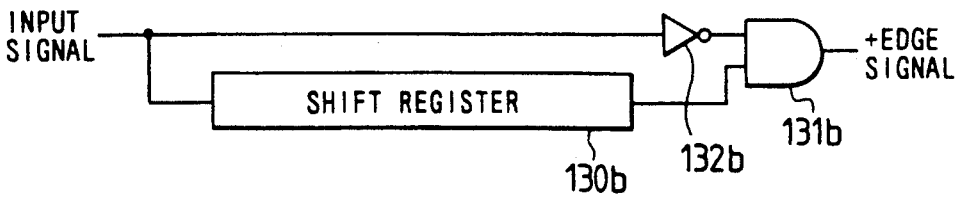

FIGS. 6(a) and 6(b) show examples of the −edge detection circuit and the +edge detection circuit which constitute edge detection circuits 29 and 30 in FIG. 1.

In FIGS. 6(a) and 6(b), two picture elements are vertically separated by shift registers 130a and 130b with a length of the number of picture elements of line sensor 13a or 13b to generate edge signals. 131a and 131b indicate AND gates, and 132a and 132b indicate invertors.

Figure 7:
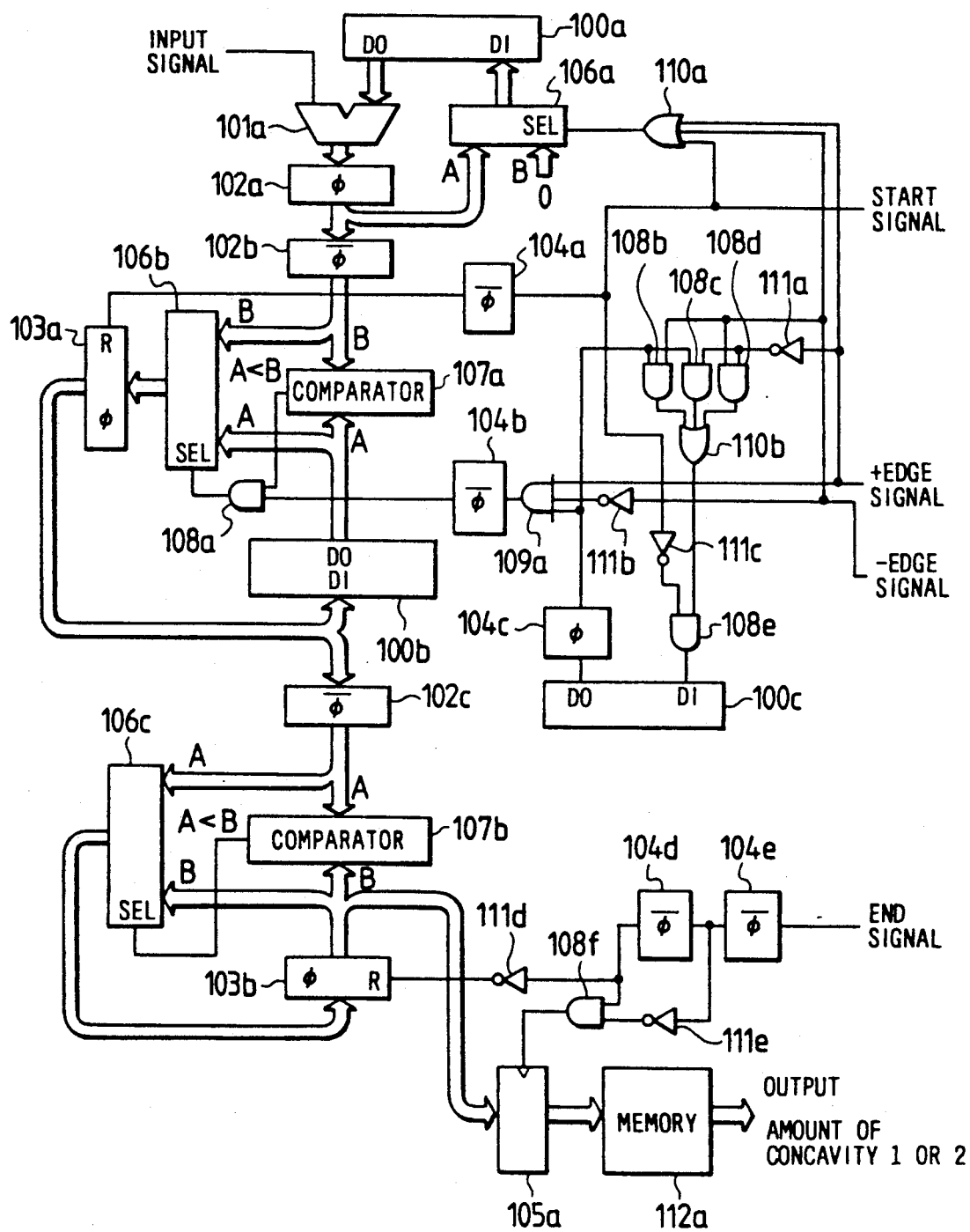
FIG. 7 shows an example of a circuit to calculate the length of a concave shadow to be used for the inspection apparatus in FIG. 1.
Figure 8:
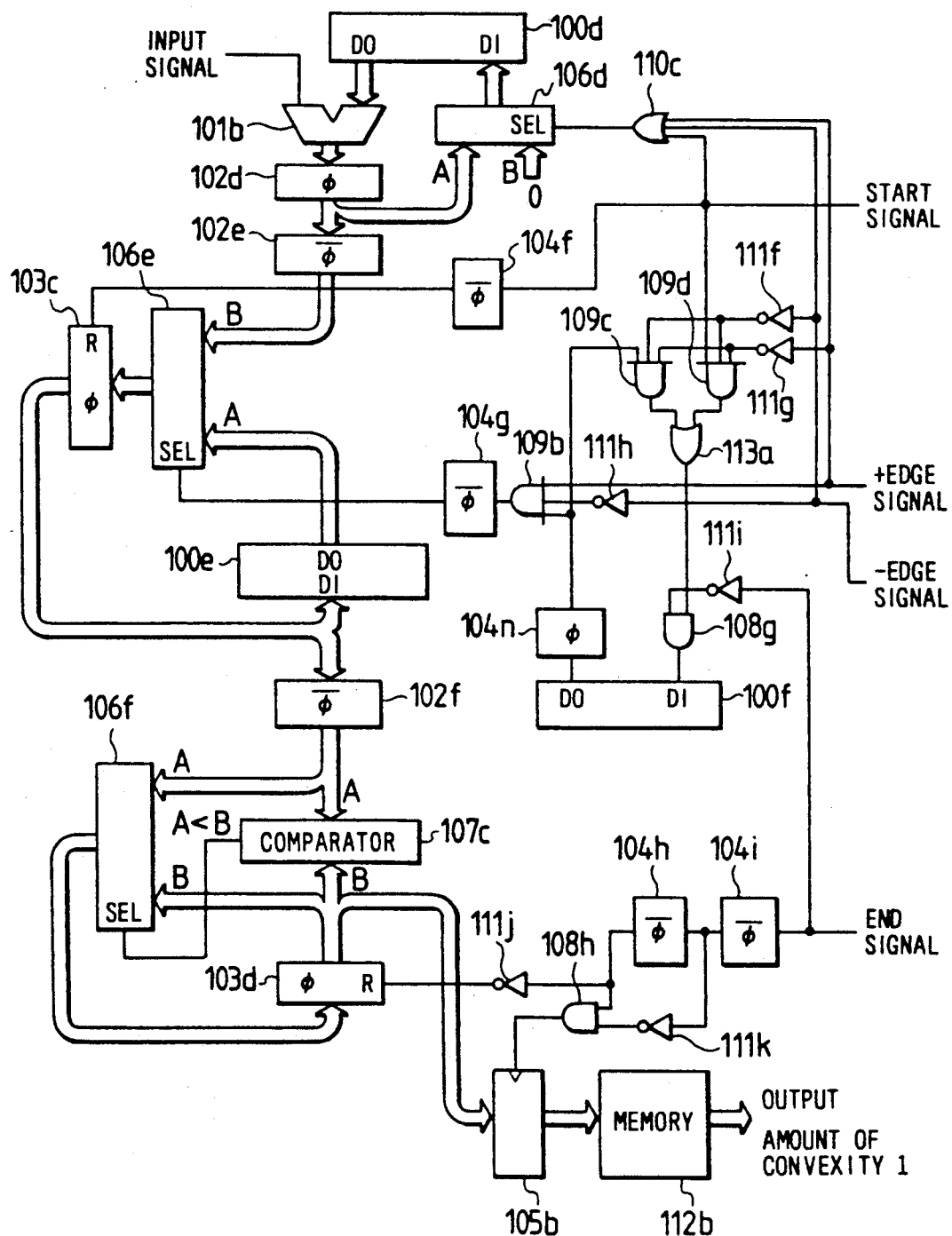
FIGS. 8 and 9 show examples of circuits to calculate the length of a convex shadow to be used for the inspection apparatus in FIG. 1.
Figure 9:
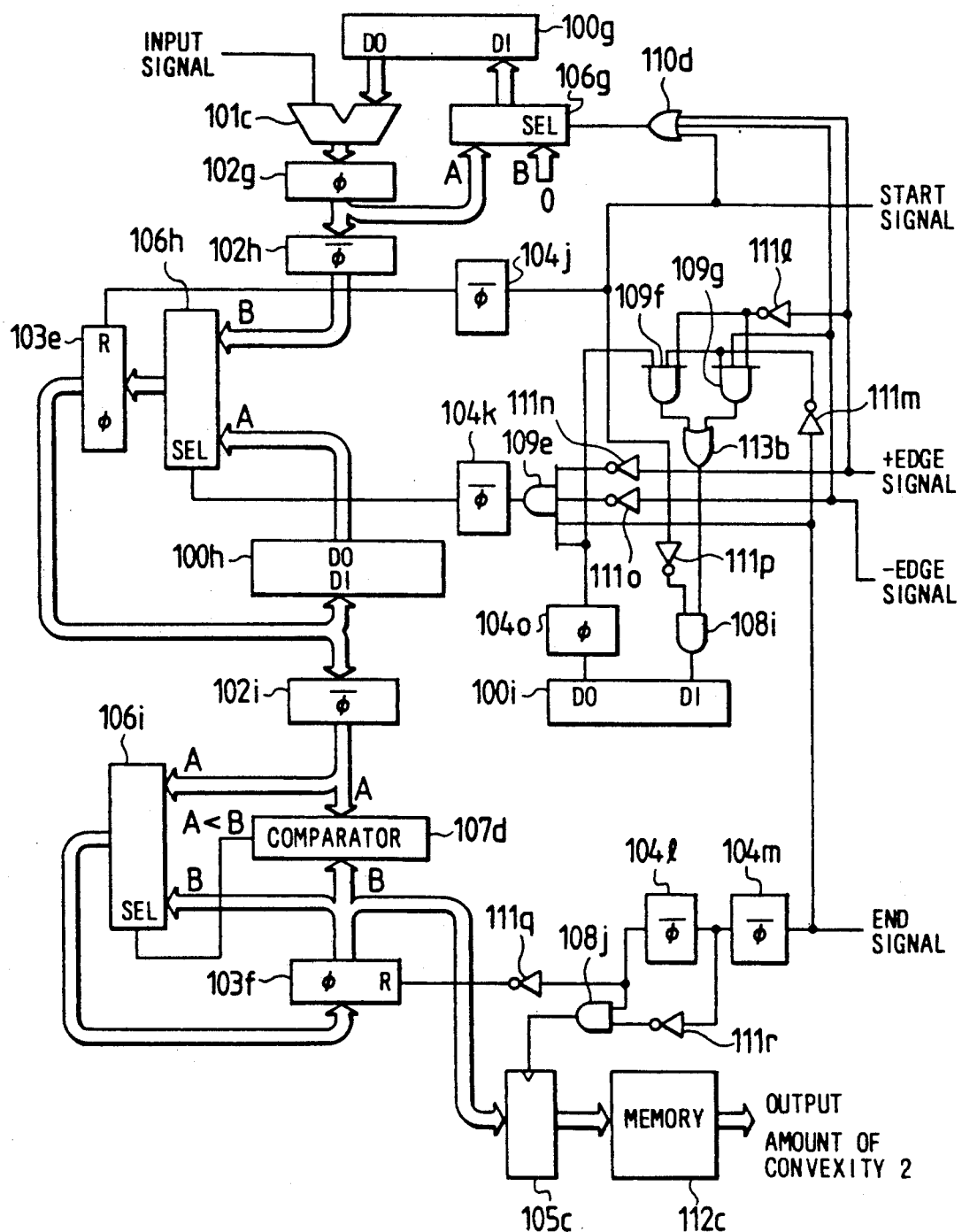

FIG. 7 shows an example of a circuit which detects amount of concavity 1 and amount of concavity 2, mentioned above. FIG. 8 shows an example of a circuit which detects amount of convexity 1, and FIG. 9 shows an example of a circuit which detects amount of convexity 2. These circuits are used in the position relationship analysis circuit 31 of FIG. 1.

In these examples, the vertical direction of each shadow in FIGS. 3(a) and 3(b) (perpendicular to the projection direction of the shadow) coincide with the picture element arrangement direction of the line sensor. Therefore, the concave or convex state is identified and the amount of concavity or convexity is detected for each picture element of the line sensor.

Descriptions of the circuit to detect the amount of concavity shown in FIG. 7 follow.

When the circuit in FIG. 7 is a detection circuit for amount of concavity 1, the input signal to be supplied to this circuit is an output signal of binarizing circuit 20 in FIG. 1 if the green sheet 1 in FIG. 1 moves in the direction of the arrow A. If the green sheet 1 moves in the direction of the arrow B, the input signal is changed to an output signal of binarizing circuit 21 in FIG. 1. When the circuit in FIG. 7 is a detection circuit for amount of concavity 2, the input signal to be supplied to this circuit is an output signal of binarizing circuit 21 in FIG. 1 if the green sheet 1 in FIG. 1 moves in the direction of the arrow A. If the green sheet 1 moves in the direction of the arrow B, the input signal is changed to an output signal of binarizing circuit 20 in FIG. 1.

Figure 10:
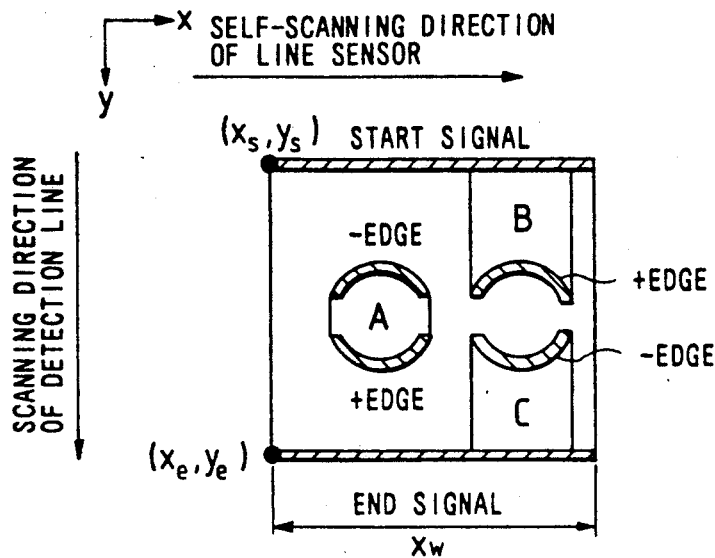
FIG. 10 shows the locations of a start signal and an end signal of the inspection apparatus in FIG. 1.

A Start signal and an End signal correspond to the upper side (the Start signal) and to the lower side (the End signal) of a rectangular area to detect the amount of concavity or convexity as shown in FIG. 10, and are generated by a detection window generation circuit which is described later. The amount of concavity detection circuit detects the maximum length of the shadow corresponding to the concave in the rectangular area which lies between the Start signal and the End signal, and stores the detected value in a memory 112a.

The input signal (binary) is added to output DO of a memory 100a with a capacity of one line image data by an adder 101a, stored in a latch 102a, and written in the same address of the memory 100a once again via selector 106a. In this case, the discrete values of the shadow lengths are stored in latches 102a and 102b. The addresses of memory 100a are incremented line by line starting with 0 in the picture element read sequence by the line sensor (the address generation circuit is not shown in the Figure). When the Start signal, +edge signal, or −edge signal is inputted, the selector 106a selects 0 and initializes the discrete values.

When AND gates 108b to 108e and 109a, an OR gate 110b, invertors 111a to 111c, a memory 100c with the capacity of one line image data, and a latch 104c are connected as shown in the Figure, a latch 104b outputs a signal which is 1 in an area A in FIG. 10. The address generation method for the memory 100c is the same as that for the memory 100a. When the output of latch 104b is 1, the output of latch 102b or the output of memory 100b is selected by the selector 106b and stored in a latch 103a depending on whether the output data A of comparator 107a is larger or smaller than data B. When A≧B, data A is stored. When A<B, data B is stored. When the output of latch 104b is 0, the output data B is selected by the selector 106b and stored in the latch 103a. The output data of latch 103a is written in the same address of memory 100b. The memory 100b is a memory with the capacity of one line image data the same as the memory 100a or the memory 100c, and the address generation method for the memory 100b is the same as that for the memory 100a or the memory 100c. By doing this, the latch 103a and a latch 102c which is connected to the latch 103a store the longest shadow length in the area A, which is enclosed by the −edge and the +edge, (more than one area may exist) in the specific x coordinate between the Start signal and the End signal in FIG. 10. The latch 103a is initialized to 0 by the Start signal beforehand.

The output data of latch 103b, which is always forced to be set to 0 for other than the End signal, is compared with the output data of latch 102c by a comparator 107b finally, and the larger data is selected by a selector 106c.

In this case, the longest shadow length in the area enclosed by the −edge and the +edge within the rectangular area between the Start signal and the End signal is outputted from the latch 103b at the end of the End signal (at the right end of the End signal in FIG. 10). The trailing edge of the End signal is detected by latches 104d and 104e, an AND gate 108f, and an inverter 111e, and the output data of latch 103b is stored in a latch 105a and then in the memory 112a one by one. By doing this, the amount of concavity in each detection window between the Start signal and the End signal is detected.

A symbol $\phi$ in FIG. 7 means that data is latched at the leading edge of a clock signal of the corresponding line sensor to each picture element, and a symbol $\overline{\phi}$ means that data is latched at the trailing edge of a clock signal. A symbol R indicates that a reset signal is inputted. The selectors 106a, 106b and 106c select data A when the SEL signal is 0 or data B when the SEL signal is 1.

The configuration and operation in FIGS. 8 and 9 are almost the same as those in FIG. 7 except the following: The circuits in FIGS. 8 and 9 are structured so that the outputs of latch 104g in FIG. 8 and latch 104k in FIG. 9 are 1 in areas B and C in FIG. 10, and a selector 106e in FIG. 8 and a selector 106h in FIG. 9 select input data according to the outputs of latches 104g and 104k.

When the circuit in FIG. 8 is a detection circuit for amount of convexity 1, the input signal to be supplied to the circuit in FIG. 8 is an output signal of binarizing circuit 20 in FIG. 1 if the green sheet 1 in FIG. 1 moves in the direction of the arrow A. If the green sheet 1 moves in the direction of the arrow B, the input signal is changed to an output signal of binarizing circuit 21 in FIG. 1. When the circuit in FIG. 9 is a detection circuit for amount of convexity 2, the input signal to be supplied to the circuit in FIG. 9 is an output signal of binarizing circuit 21 in FIG. 1 the if the green sheet 1 in FIG. 1 moves in the direction of the arrow A. If the green sheet 1 moves in the direction of the arrow B, the input signal is changed to an output signal of binarizing circuit 20 in FIG. 1.

Figure 11:
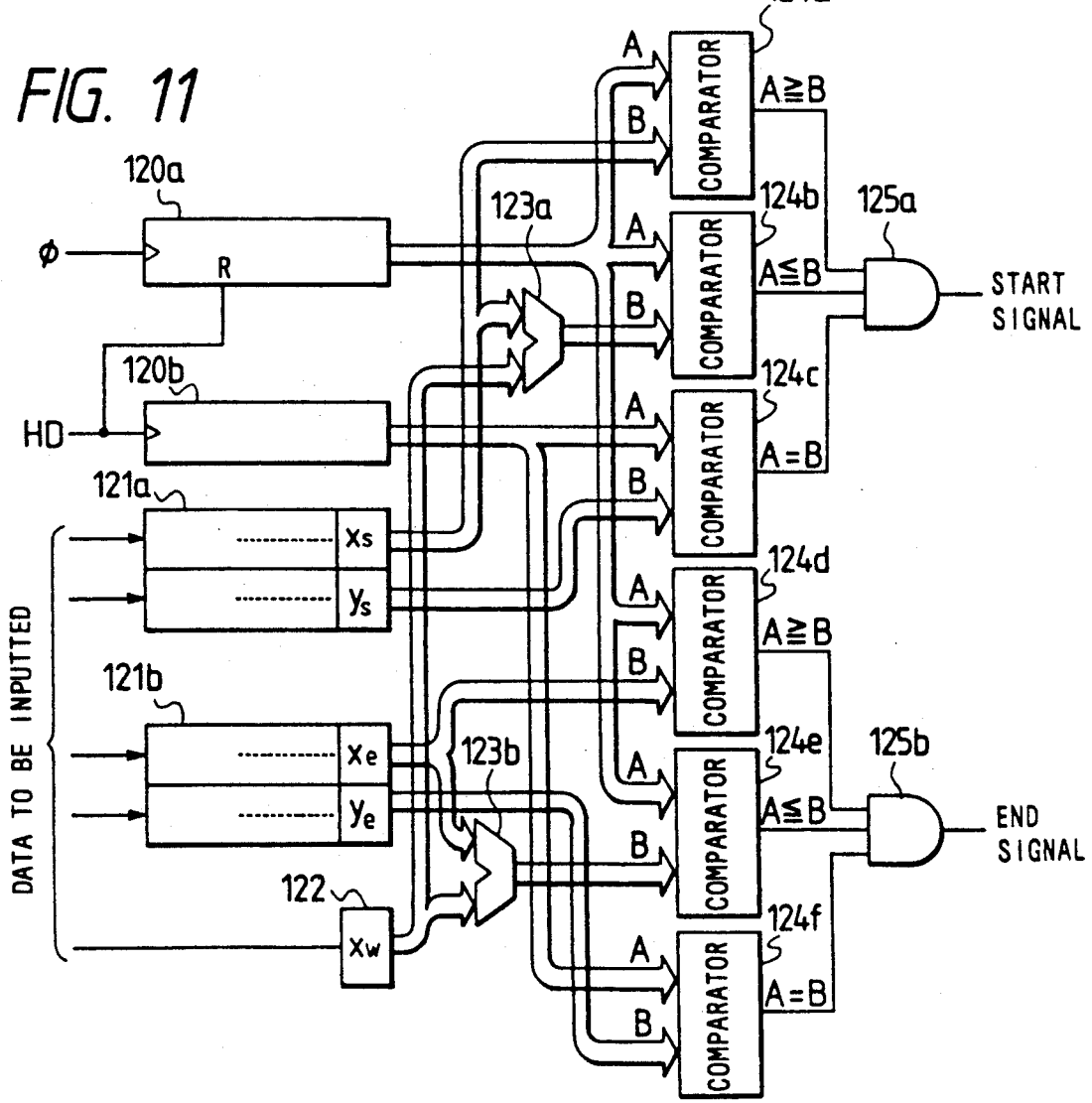
FIG. 11 shows an example of the generation circuit a start signal and an end signal of the inspection apparatus in FIG. 1.

FIG. 11 shows an example of the detection window generation circuit, or of the Start signal and End signal generation circuit. Before starting detection of the amount of concavity or convexity, the start address (xs, ys) of the Start signal is stored in a memory 121a, the start address (xe, ye) of the End signal is stored in a memory 121b, and the width (xw) of the detection window is stored in a register 122. The addresses (xs, ys) and (xe, ye) are stored in the memories in the occurrence order. Reading the data of memories 121a and 121b sequentially, the detection window generation circuit compares xs, xe, xs+xw, and xe+xw with the output data of counter 120a in the x direction, and ys and ye with the output data of counter 120b in the y direction using comparators 124a, 124d, 124b, 124e, 124c, and 124f respectively. These output data of the comparators are composed by AND gates 125a and 125b to generate the Start signal and the End signal. xs+xw and xe+xw are generated by adders 123a and 123b. A symbol in FIG. 11 indicates a clock signal of the line sensor corresponding to each picture element, and HD indicates a synchronizing signal for each line.

Four numerical values indicating amount of concavity 1, amount of concavity 2, amount of convexity 1, and amount of convexity 2 are supplied to the comparator 49 from the position relationship analysis circuit 31, and the four reference values corresponding to these four numerical values are supplied to the comparator 49 from the microcomputer 27. The comparator 49 compares and decides whether the four numerical values exceed the four corresponding reference values or not. The comparator 49 supplies four signals indicating the decisions to the decision memory 56.

The example of the position relationship analysis circuit mentioned above shows that when a plurality of objects to be detected are found on one scanning line, the area where the objects exist can be separated for detection. Therefore, the concave or convex state of a large number of objects can be detected at a high speed.

Descriptions of the defect decision method, which calculates the area, perimeter, and diameter of the via-hole filler and the shadow area for each via-hole from binarized images of the via-hole filler and shadows, using an example with images binarized by two threshold values follow.

Figure 12:
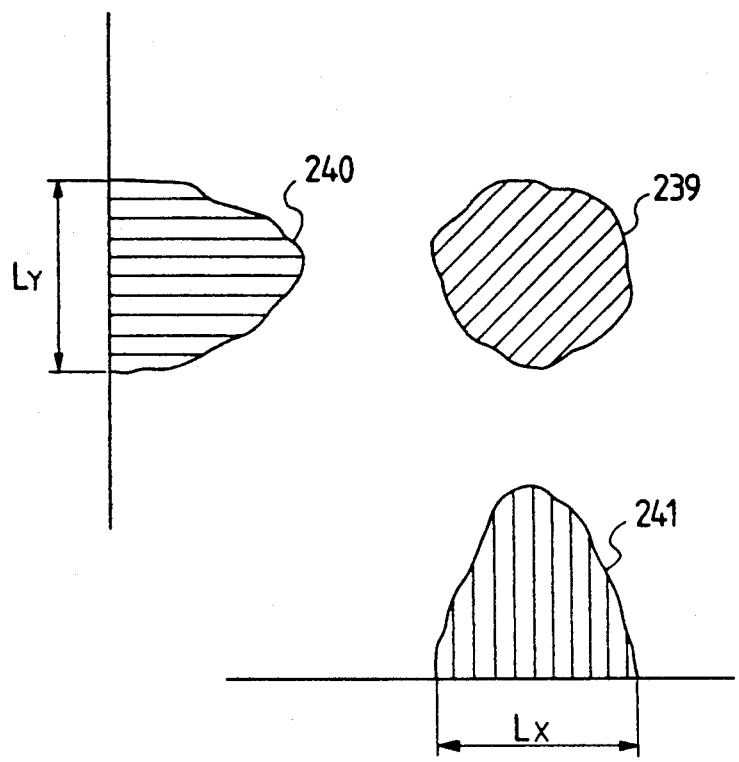
FIG. 12 illustrates the concepts on projection distribution in the inspection apparatus of FIG. 1.

FIG. 2(d) shows binary images which are binarized by the two threshold values $VH_1$ and $VH_2$. The area $SH_1$, perimeter 1, and diameters LX and LY of the via-hole filler are determined from the images binarized by the threshold value $VH_1$. The shadow area $SH_2$ is determined from the images binarized by the threshold $VH_2$. A defect decision can be given from these output data. Assuming that the area of a via-hole filler is $SH_0$, the perimeter is $l_0$, and the diameter is $L_0$, and those of a via-hole filler in the normal filled state, which is binarized by the threshold $VH_1$, are the reference values, the decision is as follows:

Good: $SH_1 = SH_0$, $l \approx LY \approx L_0$
Concave defect: $SH_1 \approx SH_0$, $SH_2 > 0$
Convex defect: $SH_1 > SH_0, SH_2 > 0$
Lack of filler defect: $SH_1 < SH_0$
Blotch defect: $SH_1 > SH_0$, $l > l_0$
Blob defect: $SH_1 > SH_0$, $l > l_0$ The apparatus shown in FIG. 1 detects the area, via-hole diameter, and perimeter from the projection distribution. An example of the detection method is shown in FIG. 12. A reference numeral 239 in FIG. 12 indicates a binary image of the via-hole filler, and reference numerals 240 and 241 indicate the projection distributions of binary image 239 in the horizontal and vertical directions. The area of the via-hole filler can be determined by integrating the value of projection distribution 240 or 241. The diameters LX and LY of the via-hole filler can be determined from the ranges where projection distributions 241 and 240 exist as shown in FIG. 12. The perimeter can be determined by extracting a contour image of the via-hole filler and calculating the area of horizontal or vertical projection distribution of the extracted contour image.

Figure 13:
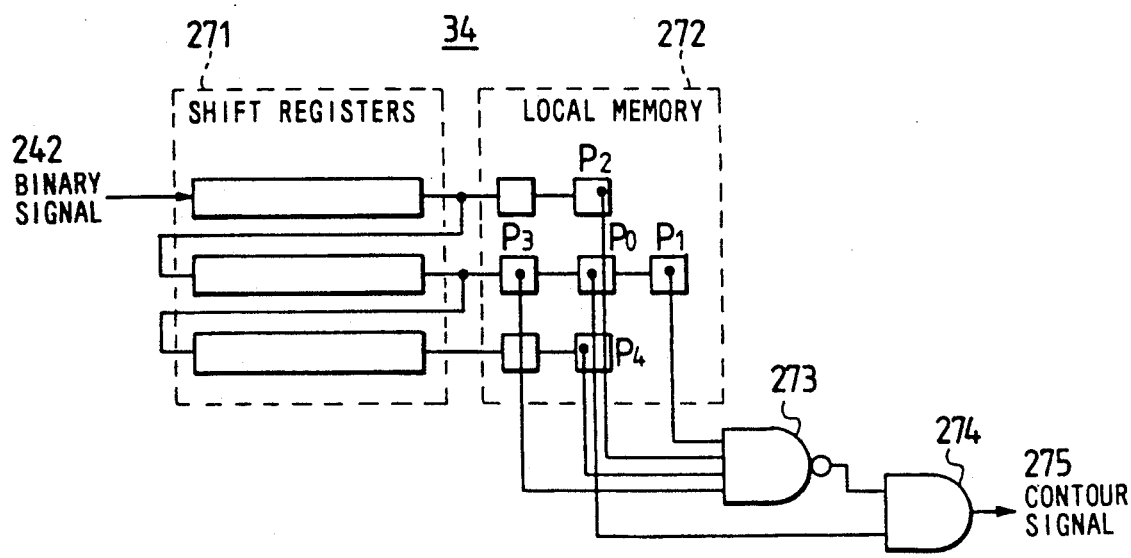
FIG. 13 shows an example of a contour extraction circuit to be used for the inspection apparatus in FIG. 1.

FIG. 13 shows a configuration example of the contour extraction circuit 34 to extract the contour signal from binary signal 242. The binary signal 242 is inputted to a shift register group 271 comprising three shift registers each of which has a length equivalent to that of one scanning line, then to a local memory 272 comprising serial-in and parallel-out shift registers. The output data of shift registers $P_1$, $P_2$, $P_3$, and $P_4$ in the local memory 272 are inputted to a NAND gate 273. The output data of NAND gate 273 and the output data of shift register $P_0$ are inputted to an AND gate 274. In this configuration, when $P_0$ is 1 and at least one of $P_1$, $P_2$, $P_3$, and $P_4$ is 0, the output data of AND gate 274 is 1 and contour signal 275 is obtained as an output of AND gate 274.

Figure 14:
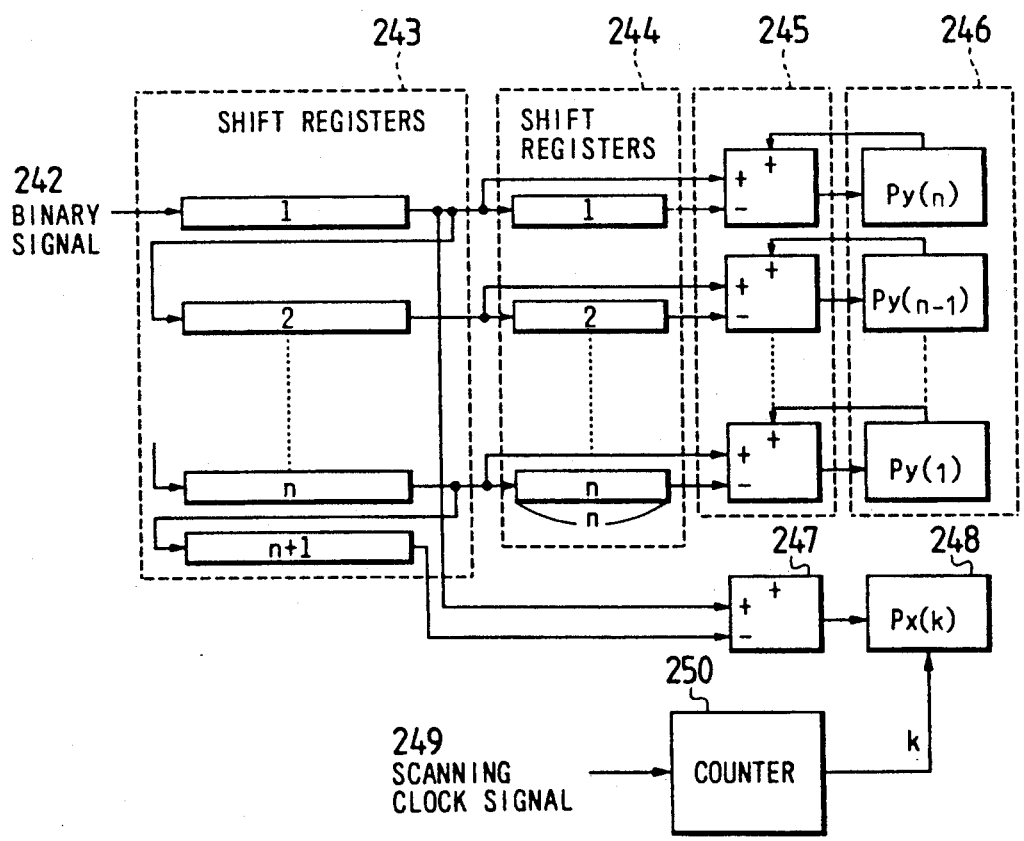
FIG. 14 shows an example of a projection distribution making circuit to be used for the inspection apparatus in FIG. 1.
Figure 15:
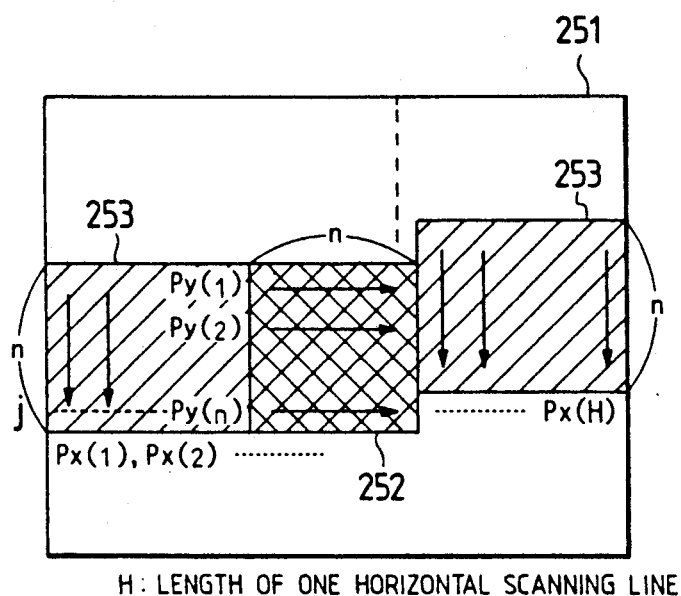
FIG. 15 illustrates the operation of the projection distribution making circuit shown in FIG. 14.

FIG. 14 shows a concrete configuration example of the projection distribution making circuits 32, 33, 39, and 41 which create projection distribution of images for each via-hole. A binary signal 242 is inputted to a shift register group 243 comprising n+1 shift registers each of which has a length equivalent to that of one scanning line of sensors 13b and 13c. The output data of the n shift registers in the group 243 are inputted to adding and subtracting circuits 245 via n shift registers 244 each of which has a length equivalent to n picture elements. The adding and subtracting circuits 245 adds each output data of the n shift registers in the shift register group 243 and each output data of horizontal projection data memories 246 and subtracts each output data of shift registers 244 from each sum. The results are inputted to horizontal projection data memories 246, and the contents of the memories are updated. The output data of the first shift register and the output data of the "n+1"th shift register in the shift register group 243 are inputted to an adding and subtracting circuit 247. Those data are added to or subtracted from the output data of a vertical projection data memory 248. The results are inputted to a vertical projection data memory 248, and the contents of the memory are updated. The vertical projection data memory 248 has a capacity equivalent to the length of one scanning line and a counter 250 counts scanning clock signal 249. The address i of the position on the scanning line, which is equivalent to the output data of shift register group 243, is specified by the output data of the counter 250. When the apparatus is structured like this, in PY(j) (j = 1, 2, 3, ..., n) of horizontal projection data memories 246, two binary signals at a distance of n+1 picture elements on the scanning line are added or subtracted, so that the binary signals for the n picture elements at the interval are added and the sum is inputted. In PX(k) of vertical projection data memory 248, the binary signals on the n scanning lines are added and the sum is inputted. Assuming that the output position of the 1st shift register in the shift register group 243 is (i, j) for a two-dimensional image 251, the distribution of area 252 is inputted to the horizontal projection data memories 246, and the distribution of area 253 (including area 252) is inputted to the vertical projection data memory 248, as shown in FIG. 15.

Figure 16:
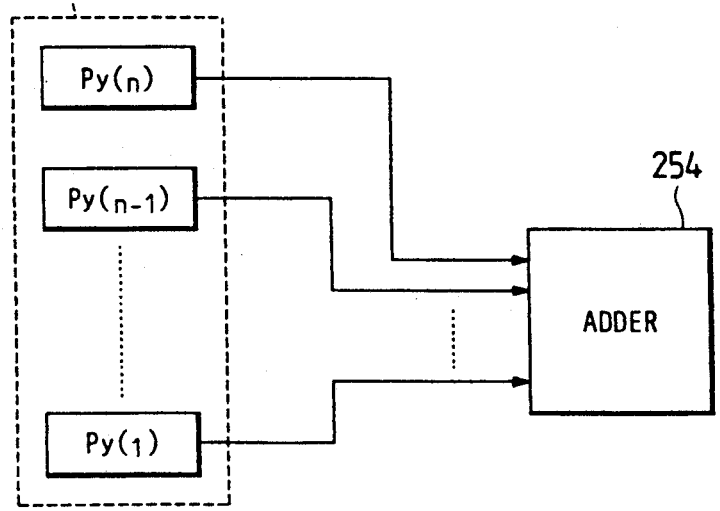
FIG. 16 shows an example of an area calculating circuit to be used for the inspection apparatus in FIG. 1.
Figure 17A:
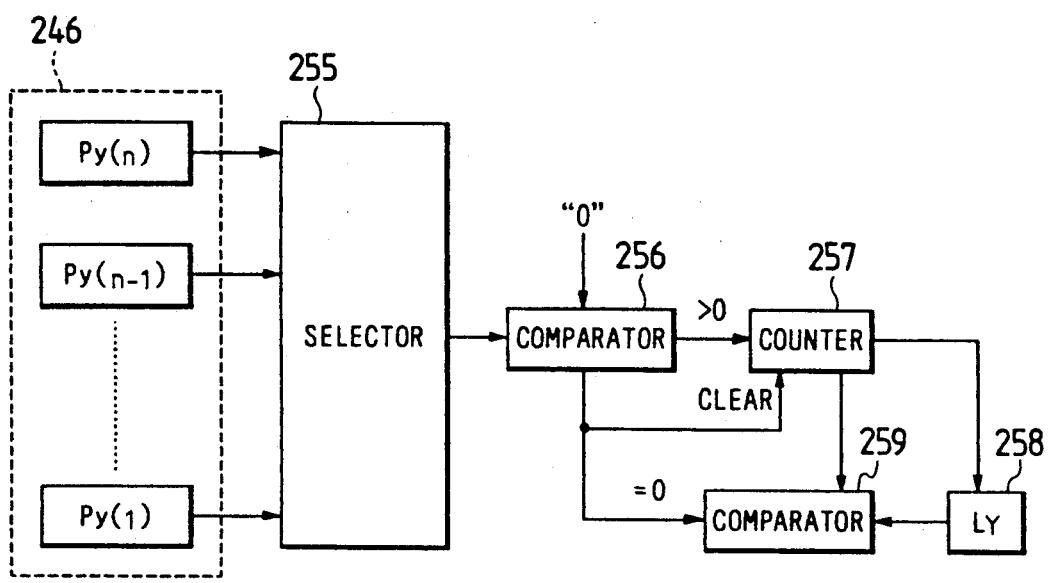
FIGS. 17(a) and 17(b) are block diagrams indicating examples of via-hole diameter calculating circuits to be used for the inspection apparatus in FIG. 1, respectively.
Figure 17B:
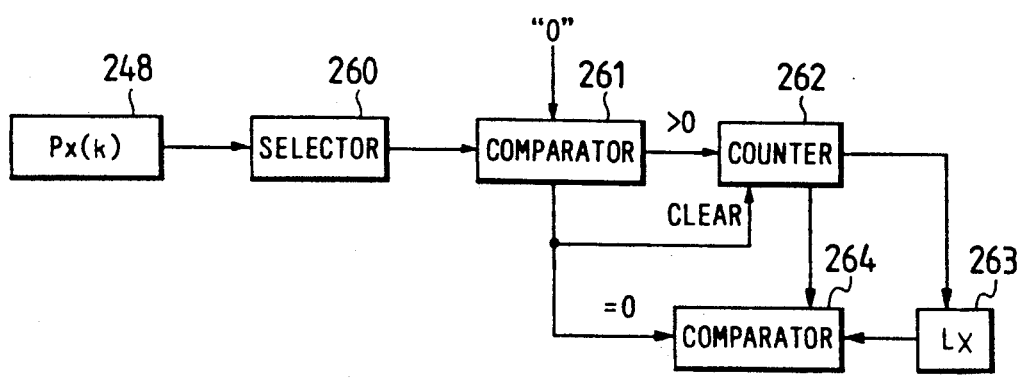

FIG. 16 shows a concrete configuration example of the area calculating circuits 35, 36, and 42 to calculate the area from those projection distributions. FIG. 16 shows an example of area calculation of the n×n-picture element area from the data in the horizontal projection data memories 246. The area can be determined by inputting the outputs of horizontal projection data memories 246 to an adder 254. FIGS. 17(a) and 17(b) show concrete configuration examples of calculation of the diameters LX and LY of the via-hole filler in the n×n-picture element area from the data in the horizontal and vertical projection data memories 246 and 248. A selector 255 in FIG. 17(a) reads the contents of PY(1), PY(2), ..., Py(n) of horizontal projection data memories 246 sequentially, and compares the values with 0 by a comparator 256. When any value is more than 0, a counter 257 is incremented by one. When the comparator 256 detects that the output data of selector 255 is 0, the values of LY register 258 and counter 257 are compared by a comparator 259. When the value of counter 257 is larger, the value is set in the LY register 258 and the counter 257 is cleared. In this configuration, the data of horizontal projection data memories 246 are not 0, and the maximum value of continuous lengths is inputted to the LY register 258 by reading horizontal projection data memories 246. A selector 260 in FIG. 17(b) reads the n contents of PX(j−n+1), PX(j−n+2), ..., PX(j) of vertical projection data memory 248 sequentially, and compares the values with 0 by a comparator 261. When any value is more than 0, a counter 262 is incremented by one. When the comparator 261 detects that the output data of selector 260 is 0, the values of LX register 263 and counter 262 are compared by a comparator 264. When the value of counter 262 is larger, the value is set in the LX register 263 and the counter 262 is cleared. In this configuration, the data of vertical projection data memory 248 are not 0, and the maximum value of continuous lengths is inputted to the LX register 263.

Figure 18:
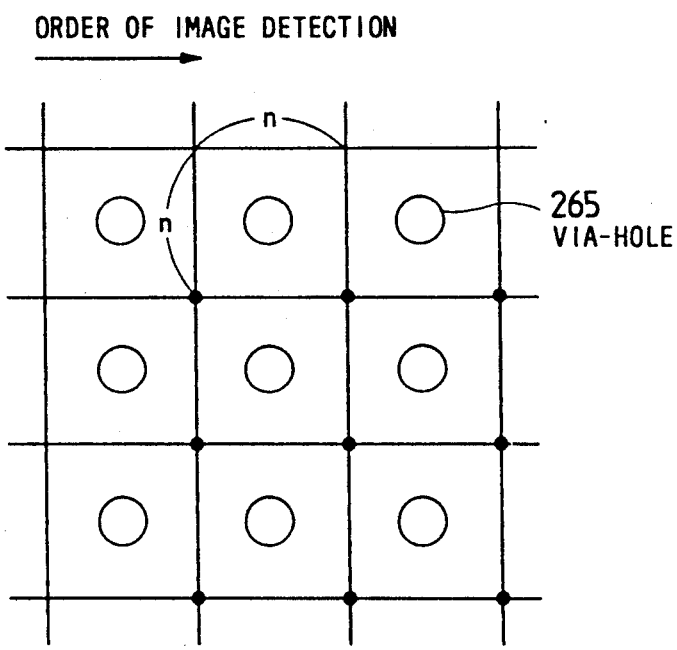
FIG. 18 shows the coordinates of the area including via-holes, for explaining a timing of the operation of each calculating circuit of the inspection apparatus in FIG. 1.

Descriptions of the operation timing, which is shown in FIG. 18, for the position relationship analysis circuit 31, area calculating circuits 35, 36, and 42, via-hole diameter calculating circuits 37 and 38, and perimeter calculating circuit 40. In FIG. 18, via-holes 265 are arranged at a fixed pitch of n and images are detected in the sequence of the arrow. The microcomputer 27 outputs the coordinates, which are indicated by black circles in FIG. 18, to the via-hole coordinate table memory 47 according to the design data, which is inputted from the floppy disk 46. The contents of via-hole coordinate table memory 47 are checked by the comparator 48 to decide whether the coordinate data matches the output position of the first shift register in the shift register group 243 shown in FIG. 14. Whenever a match is found, the microcomputer 27 activates the position relationship analysis circuit 31, area calculating circuits 35, 36, and 42, via-hole diameter calculating circuits 37 and 38, and perimeter calculating circuit 40. By doing this, the area, perimeter, and diameter of the via-hole filler can be determined from the horizontal projection distribution and vertical projection distribution in the area of n by n picture elements enclosing the via-hole 265. When a plurality of via-hole pitches are provided, it is clear that the operations mentioned above can be performed by setting the coordinates, which are indicated by black circles in FIG. 18, in the via-hole coordinate table memory 47 according to the design data.

Figure 19:
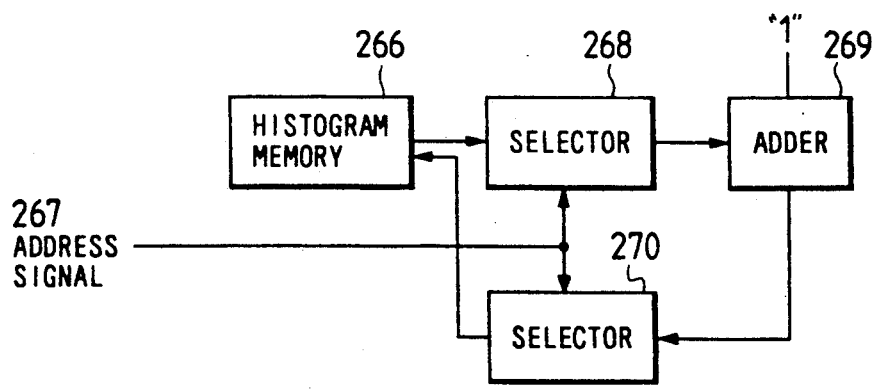
FIG. 19 is a block diagram indicating an example of a histogram generation circuit to be used for the inspection apparatus in FIG. 1.

FIG. 19 shows a concrete configuration example of the histogram generation circuits 24, 25, and 26. In FIG. 19, using the output 267 of linear sensor 13a, 13b, or 13c as an address signal, a histogram memory 266 is read by a selector 268 and incremented by +1 by an adder 269, and the sum is outputted to the same address of histogram memory 266 by a selector 270. In this configuration, each address of histogram memory 266 corresponds to the signal level, and the frequency distribution of detection signals, whose contents correspond to the frequency, can be obtained.

In the inspection apparatus of the present example, the inspection position of green sheet 1 is measured by the XY coordinate determination circuit 44. Therefore, when an inspection for the presence of a via-hole with the position information contained in the design data shows that said via-hole is not found or vice versa, it can be outputted as a defect.

The concave-convex defect detection methods described in the example mentioned above are as follows: (i) one method identifies a concave or convex from the relative position relationship of the edges of the binary image of a shadow and detects the amount of concave or convex from the shadow length and (ii) the other method detects a concave or convex from the areas of the binary images of the filler and the shadow. The method (i) of the two is effectual in identifying a concave or convex exactly. The experiment of the inventors shows that a concave or convex of about 10 μm length generated on a via-hole filler or a green sheet can be exactly identified and detected. The method (ii) is effectual in realizing an inexpensive and simple configuration of the apparatus for detecting a concave or convex because said apparatus comprises only one detection system, though the detection sensitivity is lower than that of the method (i). The experiment of the inventors shows that a concave or convex of about 20 μm length generated on a via-hole filler or a green sheet can be exactly detected.

The inspection apparatus described in the present example has a structure of three detection systems. When a comparison of shadow areas in the method (ii) is used for detecting a concave defect or convex defect, one sensor can identify and detect a concave defect, convex defect, lack of filler defect, blotch defect, and/or blob defect shown in FIG. 2. When only the line sensor 13c is used and the binarizing circuits 21 and 22 are connected to the output terminals of shading correction circuit 19 in FIG. 1, all the defects shown in FIG. 2 can be detected with only the line sensor 13c, producing satisfactory results in realizing an inexpensive and simple configuration of the apparatus for identification and detection of defects.

Figure 20A:
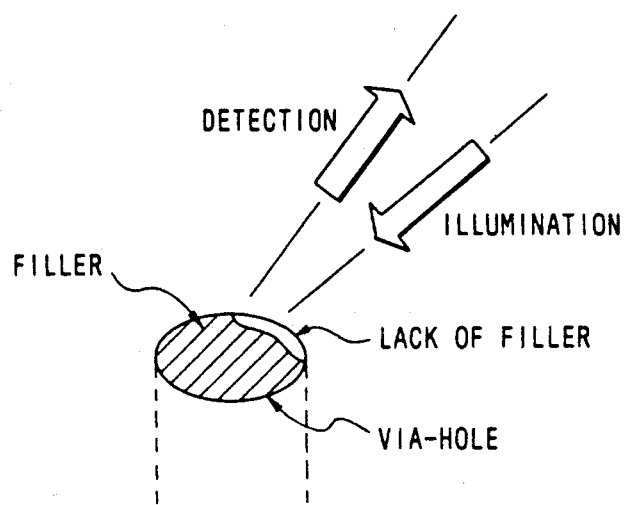
FIG. 20(a) is a perspective view indicating the lack of filler state in a via-hole.
Figure 20B:
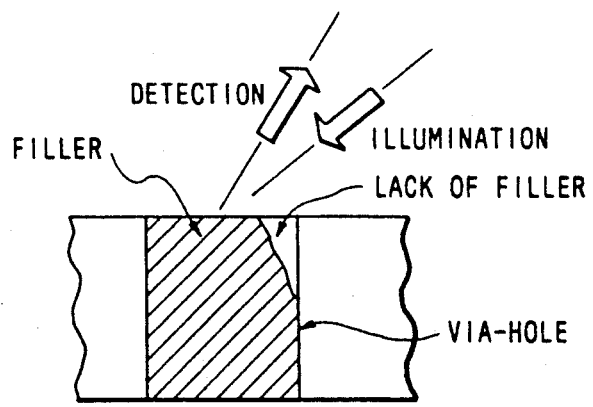
FIG. 20(b) shows a sectional view of the via-hole and the filler therein shown in FIG. 20(a).
Figure 21:
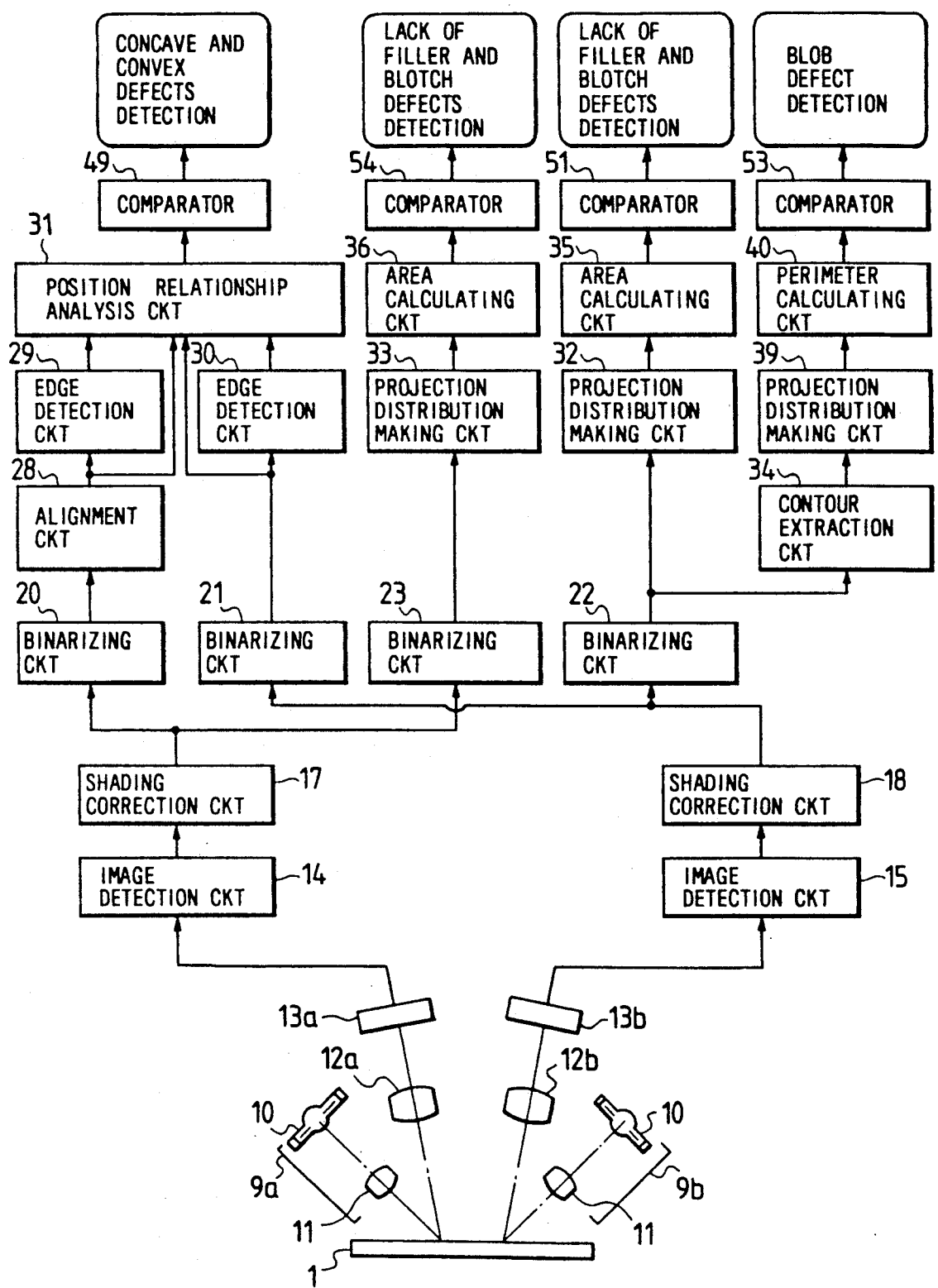
FIG. 21 is a block diagram indicating another example of the inspection apparatus for carrying out the method provided by the present invention.

Fatal defects of the defects shown in FIG. 2, which may cause disconnection, are a concave defect and a lack of filler defect. FIG. 20 (a) is a perspective view of a via-hole with a lack of filler, and FIG. 20(b) is a sectional view of the via-hole shown in FIG. 20(a). In the example of FIG. 1, the lack of filler defect is detected in only one direction. Therefore, the detection sensitivity for such a defect that a part of the filler in a via-hole is lacking as shown in FIGS. 20(a) and 20(b) is low. To prevent such a reduction in detection sensitivity, it is desirable to use a configuration of detection in two oblique directions. This method is also effectual in improving the detection capability for a lack of filler defect. The configuration in FIG. 21 can be realized by using the circuits of the example of the apparatus shown in FIG. 1, except that the lenses 12a and 12b and the line sensors 13a and 13b are arranged in the obliquely upper part.

In the embodiments of the present invention mentioned above, when a plurality of objects to be detected exist on one scanning line of a linear sensor, the area, where the objects exist, can be separated for detection. Therefore, a large number of objects can be detected at a high speed at a time.

The present invention allows a concave defect to be detected by analyzing the shadow position relationship to identify the concave or convex state of a filler and a lack of filler defect to be detected by illuminating the wall of a via-hole. Therefore, the present invention is effectual in identifying and inspecting a concave defect and lack of filler defect exactly, which are major filler defects causing defective continuity.

The present invention also allows a defect to be decided by analyzing the defect contents in each area corresponding to each via-hole. Therefore, the present invention is effectual in inspecting a large-scale circuit board containing high density via-holes at a high speed.

We claim:

1. A method for inspecting the filled state of a plurality of via-holes which pass through a circuit board from a surface thereof to the opposite surface and are filled with a substance whose electrical characteristics differ from the electrical characteristics of said circuit board, said method comprising the steps of: detecting an optical image of the surface of said circuit board having the plurality of via-holes filled with the substance; detecting a concave or convex state of the filler in each via-hole from each image of the fillers in said via-holes in the detected optical image of said surface; and deciding whether the filler is in the concave state or convex state on the basis of the detection results.

2. A method for inspecting the filled state of a plurality of via-holes which pass through a circuit board from a surface thereof to the opposite surface and are filled with a substance whose electrical characteristics differ from the electrical characteristics of said circuit board, said method comprising the steps of: irradiating light to the surface of said circuit board in a plurality of directions so as to generate shadows depending on a concave or convex state of the fillers in the via-holes; detecting independently optical images of a plurality of shadows of a first via-hole generated by light irradiation in said plurality of directions; identifying whether the filler in said first via-hole is in the concave state or convex state according to a positional relationship of the detected images of said shadows; and detecting lengths of the detected images of said shadows and deciding whether the concave state of the filler in the via-hole is within a predetermined allowance according to the detection results.

3. A method for inspecting the filled state of a plurality of via-holes which pass through a circuit board from a surface thereof to the opposite surface and are filled with a substance whose electrical characteristics differ from the electrical characteristics of said circuit board, said method comprising the steps of: irradiating light to a plurality of positions different from each other on the surface of the circuit board in a plurality of directions different form each other so as to generate shadows depending on a concave or convex state of the fillers in the via-holes; detecting independently optical images of a plurality of shadows of a via-hole generated by light irradiation in said plurality of directions; identifying whether the filler in one of the via-holes is in the concave state or convex state on the basis of a positional relationship of the detected images of said shadows; and detecting lengths of the detected images of said shadows and deciding whether the concave state of the filler in said one of the via-holes is within a predetermined allowance according to the detection results.

4. A method for inspecting the filled state of a plurality of via-holes which pass through a circuit board from a surface thereof to the opposite surface and are filled with a substance whose electrical characteristics differ from the electrical characteristics of said circuit board, said method comprising the steps of: irradiating light to the surface of the circuit board so as to make the brightness of an image of the wall of a via-hole different from the brightness of an image of the filler in the via-hole; detecting an optical image of the surface of said circuit board irradiated by said light; detecting an area of each image of the fillers in said via-holes, existing in the detected image of said surface; and deciding that the amount of filler in the via-hole corresponding to said each image of the fillers is lacking when the detected area of said each image of the fillers is smaller than a predetermined value.

5. A method according to claim 4, wherein light is irradiated to the surface of said circuit board so as to make the brightness of said image of the wall of the via-hole different from the brightness of the image of the surface of said circuit board.

6. A method according to claim 4, wherein light is irradiated to the surface of said circuit board so as to make the brightness of the image of the surface of said circuit board higher than the brightness of said image of the filler in the via-hole and the brightness of said image of the wall of the via-hole higher than the brightness of said image of the surface of said circuit board.

7. A method for inspecting the filled state of a plurality of via-holes which pass through a circuit board from a surface thereof to the opposite surface and are filled with a substance whose electrical characteristics differ from the electrical characteristics of said circuit board, said method comprising the steps of: irradiating light to the surface of the circuit board in a plurality of directions so as to generate shadows depending on a concave or convex state of the fillers in the via-holes; detecting an optical image of the surface of said circuit board irradiated by said light; detecting one side boundary of each of the shadows of one via-hole, which exist in the detected optical image of said surface and are generated by light irradiation in said plurality of directions; identifying whether the filler in said one via-hole is in the concave state or convex state on the basis of a mutual position relationship of the detected boundaries; detecting a length of said each of the shadows and deciding whether the concave state or convex state of the filler is within a predetermined allowance according to the length detection results; and detecting an area of an image of the filler according to differences between the brightness of the board surface or of the via-hole wall and the brightness of the filler in the via-hole in the detected optical image of said surface, and deciding whether an amount of the filler in the via-hole is sufficient according to the detected area of the image of the filler.

8. A method according to claim 7, wherein said shadows in said optical image are identified by using a plurality of binarized image signals which are obtained by binarizing an image signal representing said optical image by a plurality of threshold values different from each other.

9. A method according to claim 7, wherein images of said fillers in said optical image are identified by using a plurality of binarized image signals which are obtained by binarizing an image signals representing said optical image by a plurality of threshold values different from each other.

10. A method for inspecting the filled state of a plurality of via-holes which pass through a circuit board from a surface thereof to the opposite surface and are filled with a substance whose electrical characteristics differ from the electrical characteristics of said circuit board, said method comprising the steps of: detecting an optical image of the circuit board having the plurality of via-holes filled with the substance; dividing the detected optical image into a plurality of image areas each area containing an image of a via-hole respectively; analyzing the image existing in each of said image areas; and deciding whether a filled state of the via-hole whose image exists in each of said image areas is sufficient on the basis of the analytical results.

11. An apparatus for inspecting the filled state of a plurality of via-holes which pass through a circuit board from a surface thereof to the opposite surface and are filled with a substance whose electrical characteristics differ from the electrical characteristics of said circuit board, said apparatus comprising: means for detecting an optical image of the surface of the circuit board having the plurality of via-holes filled with the substance; means for detecting a concave or convex state of the fillers in each via-hole from each image of the filler in said via-holes in the detected optical image of said surface; and means for deciding whether the concave state or convex state of the filler is within a predetermined allowance on the basis of the detection results.

12. An apparatus for inspecting the filled state of a plurality of via-holes which pass through a circuit board from a surface thereof to the opposite surface and are filled with a substance whose electrical characteristics differ from the electrical characteristics of said circuit board, said apparatus comprising: means for irradiating light to the surface of the circuit board in a plurality of directions so as to generate shadows depending on a concave or convex state of the fillers in the via-holes; means for detecting independently optical images of a plurality of shadows of a first via-hole generated by light irradiation in said plurality of directions; means for identifying whether the filler in said first via-hole is in the concave state or convex state on the basis of a positional relationship of the detected images of said shadows; and means for calculating lengths of the detected images of said shadows and deciding whether the concave state of the filler in the via-hole is within a predetermined allowance according to the calculation results.

13. An apparatus for inspecting the filled state of a plurality of via-holes which pass through a circuit board from a surface thereof to the opposite surface and are filled with a substance whose electrical characteristics differ from the electrical characteristics of said circuit board, said apparatus comprising: means for irradiating light to a plurality of positions different from each other on the surface of the circuit board in a plurality of directions different from each other so as to generate shadows depending on a concave or convex state of the fillers in the via-holes; means for detecting independently optical images of a plurality of shadows of a first via-hole generated by light irradiation in said plurality of directions; means for identifying whether the filler in said first via-hole is in the concave state or convex state on the basis of a positional relationship of the detected images of said shadows; and means for calculating lengths of the detected images of said shadows and deciding whether the concave state of the filler in the via-hole is within a predetermined allowance according to the calculation results.

14. An apparatus for inspecting the filled state of a plurality of via-holes which pass through a circuit board from a surface thereof to the opposite surface and are filled with a substance whose electrical characteristics differ from the electrical characteristics of said circuit board, said apparatus comprising: means for irradiating light to the surface of the circuit board so as to make the brightness of an image of the wall of a via-hole different from the brightness of an image of the filler in the via-hole; means for detecting an optical image of the surface of said circuit board irradiated by said light; means for calculating an area of each image of the fillers in said via-holes in the detected image of said surface; and decision means for deciding that the filler in the via-hole corresponding to said each image of the fillers is lacking when the calculated area of said each image of the fillers is smaller than a predetermined value.

15. An apparatus according to claim 14, wherein said illumination means irradiates light to the surface of said circuit board so as to make the brightness of said image of the wall of the via-hole different from the brightness of the image of the surface of said circuit board.

16. An apparatus according to claim 14, wherein said illumination means irradiates light to the surface of said circuit board so as to make the brightness of the image of the surface of said circuit board higher than the brightness of said image of the filler in the via-hole and the brightness of said image of the wall of the via-hole higher than the brightness of said image of the surface of said circuit board.

17. An apparatus for inspecting the filled state of a plurality of via-holes which pass through a circuit board from the surface thereof to the opposite surface and are filled with a substance whose electrical characteristics differ from the electrical characteristics of said circuit board, said apparatus comprising: means for irradiating light to the surface of the circuit board in a plurality of directions so as to generate shadows depending on a concave or convex state of the fillers in the via-holes; means for detecting an optical image of the surface of the circuit board irradiated by said light; means for detecting one side boundary of each of the shadows of a first via-hole, which exist in the detected optical image of said surface and are generated by light irradiation in said plurality of directions; means for identifying whether the filler in said first via-hole is in the concave state or convex state on the basis of a mutual position relationship of the detected boundaries; means for calculating a length of said each of shadows and deciding whether the concave state or convex state of the filler is within a predetermined allowance according to the calculation results; and means for detecting an image of the filler according to differences between the brightness of the board surface or of the via-hole wall and the brightness of the filler in the via-hole in the detected optical image of said surface, and deciding whether the amount filler in the via-hole is sufficient according to the detection results.

18. An apparatus for inspecting the filled state of a plurality of via-holes which pass through a circuit board from a surface thereof to the opposite surface and are filled with a substance whose electrical characteristics differ from the electrical characteristics of said circuit board, said apparatus comprising: means for detecting an optical image of the circuit board having the plurality of via-holes filled with the substance; means for dividing said detected optical image into a plurality of image areas, each said area containing an image of a via-hole respectively; means for analyzing the image existing in each of said image areas; and decision means for deciding whether a filled state of the via-hole whose image exists in said each of image areas is sufficient on the basis of the output of said analytical means.

* * * * *

UNITED STATES PATENT AND TRADEMARK OFFICE
CERTIFICATE OF CORRECTION

PATENT NO. : 5,015,097

DATED : May 14, 1991

INVENTOR(S) : Mineo Nomoto et al

It is certified that error appears in the above-identified patent and that said Letters Patent is hereby corrected as shown below:

| Column | Line | |
|---|---|---|
| 1 | 33 | After "defects" insert --,--. |
| 3 | 24 | After "symbol" change "()" to --min ()--. |
| 3 | 25 | After "parentheses" insert --is to be selected.--. |
| 4 | 21 | After "circuit" insert --of--. |
| 5 | 3 | Before "vertically" insert --a--; after "upper" insert --point,--. |
| 6 | 58 | After "example" insert --,--. |
| 7 | 40 | Change '".""' to --"."--. |
| 8 | 1 | Do not italicize "indicate". |
| 8 | 2 | Do not italicize "invertors". |
| 8 | 67 | After "104b" do not italicize "is". |
| 10 | 10 | After "symbol" insert --∅--. |
| 10 | 49 | Change "$1 \approx LY \approx L_o$" to --$1 \fallingdotseq l_o$, $LX \fallingdotseq LY \fallingdotseq L_o$--. |
| 10 | 50 | Change "$SH_1 \approx SH_o$" to --$SH_1 \fallingdotseq SH_o$--. |
| 14 | 57 | Change "form" to --from--. |

UNITED STATES PATENT AND TRADEMARK OFFICE
CERTIFICATE OF CORRECTION

PATENT NO. : 5,015,097

DATED : May 14, 1991

INVENTOR(S) : Mineo Nomoto et al

It is certified that error appears in the above-identified patent and that said Letters Patent is hereby corrected as shown below:

| Column | Line | |
|--------|------|---|
| 3 | 19 | Change "When" to --when--. |
| 3 | 49 | Change "fects." to --fect.--. |
| 3 | 57 | Change "defects" to --defect--. |
| 5 | 16 | After "from" insert --an--. |
| 7 | 27 | Change "an FIFO" to --a FIFO--. |
| 9 | 54 | After "FIG. 1" delete "the". |
| 12 | 37 | After "circuit 40" insert --follow--. |
| 15 | 68 | After "binarizing" delete "an". |

Signed and Sealed this

Sixteenth Day of February, 1993

Attest:

STEPHEN G. KUNIN

Attesting Officer

Acting Commissioner of Patents and Trademarks